(12) United States Patent
Åkerfeldt (10) Patent No.: US 8,088,143 B2
(45) Date of Patent: Jan. 3, 2012

(54) CLOSURE DEVICE

(75) Inventor: Dan Åkerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1305 days.

(21) Appl. No.: 10/994,519

(22) Filed: Nov. 23, 2004

(65) Prior Publication Data
US 2005/0131459 A1    Jun. 16, 2005

Related U.S. Application Data (63) Continuation-in-part of application No. 10/166,725, filed on Jun. 12, 2002, now Pat. No. 6,939,363.

(51) Int. Cl.
*A61B 17/10* (2006.01)
*A61B 17/08* (2006.01)
*A61D 1/00* (2006.01)

(52) U.S. Cl. .......................... 606/213; 606/139

(58) Field of Classification Search ............... 606/108, 606/213, 214, 139; 604/59, 60, 64, 73, 93.01, 604/187, 195–197
See application file for complete search history.

(56) References Cited

U.S. PATENT DOCUMENTS

| | | | |
|---|---|---|---|
| 3,871,099 A * | 3/1975 | Kahn | ................ 433/224 |
| 4,744,364 A | 5/1988 | Kensey | |
| 4,852,568 A | 8/1989 | Kensey | |
| 4,890,612 A | 1/1990 | Kensey | |
| 5,046,497 A | 9/1991 | Millar | |
| 5,061,274 A | 10/1991 | Kensey | |
| 5,108,421 A | 4/1992 | Fowler | |
| 5,357,978 A * | 10/1994 | Turk | ................ 600/585 |
| 5,391,183 A | 2/1995 | Janzen et al. | |
| 5,437,631 A * | 8/1995 | Janzen | ................ 604/506 |
| 5,643,318 A | 7/1997 | Tsukernik et al. | |
| 5,649,959 A * | 7/1997 | Hannam et al. | ............ 606/213 |
| 5,725,498 A | 3/1998 | Janzen et al. | |
| 5,741,223 A | 4/1998 | Janzen et al. | |
| 5,830,130 A | 11/1998 | Janzen et al. | |

(Continued)

FOREIGN PATENT DOCUMENTS

| | | |
|---|---|---|
| EP | 1 371 333 B1 | 5/2004 |
| WO | WO 00/33744 A1 | 6/2000 |

OTHER PUBLICATIONS

Dan Akerfeldt, U.S. PTO Office Action. U.S. Appl. No. 10/997,858, Jan. 12, 2007, 18 pgs.

(Continued)

*Primary Examiner* — Corrine M McDermott
*Assistant Examiner* — Dianne Dornbusch
(74) *Attorney, Agent, or Firm* — Foley & Lardner LLP (57) ABSTRACT

The invention provides a closure device (1) for sealing an incision channel leading through a vessel wall and into the vessel. The closure device (1) comprises a haemostatic material (3), which is contained in the distal end of an elongated insertion assembly (2). The insertion assembly (2), which comprises a stationary part (4) and a retractable part (5) being slidably movable with regard to each other, is adapted to be attached to an introducer (7) being in position in the incision channel, so that the insertion assembly (2) can be slid along the introducer (7) until the distal end of the insertion assembly (2) is in contact with the vessel wall, where the haemostatic material (3) is delivered in the incision channel by a retracting movement of the retractable part (5).

14 Claims, 6 Drawing Sheets

U.S. PATENT DOCUMENTS

| | | | |
|---|---|---|---|
| 5,902,331 A * | 5/1999 | Bonner et al. | 600/585 |
| 5,948,425 A | 9/1999 | Janzen et al. | |
| 6,117,145 A | 9/2000 | Wood et al. | |
| 6,277,094 B1 | 8/2001 | Schendel | |
| 6,325,789 B1 | 12/2001 | Janzen et al. | |
| 6,334,865 B1 * | 1/2002 | Redmond et al. | 606/213 |
| 6,368,341 B1 | 4/2002 | Abrahamson | |
| 6,475,177 B1 | 11/2002 | Suzuki | |
| 6,610,069 B2 | 8/2003 | Euteneuer et al. | |
| 6,939,363 B2 | 9/2005 | Akerfeldt | |
| 2002/0032432 A1 | 3/2002 | Nash et al. | |
| 2005/0080452 A1 | 4/2005 | Akerfeldt | |

OTHER PUBLICATIONS

Dan Akerfeldt, U.S. PTO Office Action. U.S. Appl. No. 10/997,858, Jul. 12, 2007, 8 pgs.

Dan Akerfeldt, U.S. PTO Office Action. U.S. Appl. No. 10/997,858, Dec. 4, 2007, 7 pgs.

Dan Akerfeldt, U.S. PTO Office Action. U.S. Appl. No. 10/997,858, Jul. 22, 2008, 7 pgs.

Dan Akerfeldt, U.S. PTO Office Action. U.S. Appl. No. 10/997,858, Apr. 2, 2009, 10 pgs.

Dan Akerfeldt, USPTO Office Action U.S. Appl. No. 10/997,858, Nov. 9, 2009, 10 pages.

Dan Akerfeldt, USPTO Office Action, U.S. Appl. No. 10/997,858, Feb. 12, 2010, 10 pages.

Dan Akerfeldt, USPTO Office Action, U.S. Appl. No. 10/997,858, Jul. 27, 2010, 11 pages.

Dan Äkerfeldt, USPTO Office Action, U.S. Appl No. 10/997,858, Mar. 29, 2011, 11 pages.

Dan Akerfeldt, USPTO Office Action, U.S. Appl. No. 10/997,858, Sep. 22, 2011, 11 pages.

* cited by examiner

CLOSURE DEVICE

CROSS-REFERENCE TO RELATED PATENT APPLICATIONS

This application is a continuation-in-part of U.S. application Ser. No. 10/166,725, filed Jun. 12, 2002, now U.S. Pat. No. 6,939,363, and entitled "Closure Device." The entire contents of this application are incorporated herein by reference.

BACKGROUND OF THE INVENTION

The present invention relates generally to a closure device for sealing a percutaneous puncture in a vessel, in particular a closure device with which haemostatic material is introduced in the incision channel leading to the puncture hole in the vessel wall, thereby sealing the percutaneous puncture without obstructing the flow inside the vessel and without the risk that the haemostatic material unintentionally is introduced into the vessel.

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like. After the completion of the medical procedure, there will be an incision or a wound in the wall of the blood vessel corresponding to the size of the introducer. The bleeding from the wound, which is the result of such a surgical operation, may be stopped by applying direct pressure on the wound. However, applying external pressure on the wound will require assistance of additional medical personnel and may also obstruct the flow of blood through the vessel.

U.S. Pat. No. 4,744,364 and U.S. Pat. No. 4,852,568, both of which are granted to Kensey Nash Corp., disclose how a closure means can be inserted into a blood vessel and then retracted in such a way that the engagement surface of the closure means haemostatically engages the inner surface of the blood vessel contiguous with the puncture, thereby stopping the bleeding from the puncture wound. In U.S. Pat. No. 4,890,612, which is also granted to Kensey Nash Corp., a sealing device comprises a plug means having a holding portion to be positioned in engagement with the inner surface of a vessel and a sealing portion formed of a foam material that extends into the punctured vessel to engage tissue contiguous therewith to seal the puncture wound.

As is recognized in U.S. Pat. No. 6,368,341, which is granted to Abrahamson, a drawback with the types of sealing devices described in the above-mentioned U.S. Pat. Nos. 4,744,364, 4,852,568 and 4,890,612 is that an intra-arterial sealing device extending into a blood vessel may obstruct the flow of blood therethrough. The sealing device according to U.S. Pat. No. 6,368,341 comprises a haemostatic closure device and a locating device having one or several locating members to be positioned against the inner surface of the vessel wall. The locating members are designed to provide a sufficient amount of resistance against retracting movement, so that a user is provided with an indication that the locating members are in contact with the inner vessel wall. When correctly positioned, the haemostatic closure device, which may include a clotting agent, is in the incision channel outside the vessel wall and there are no portions extending into the vessel, where such portions may obstruct the flow of blood.

SUMMARY OF THE INVENTION

However, a drawback with this sealing device is the potential risk that the locating members damage the inner vessel wall during the positioning operation, i.e. when a user retracts the locating device until he or she feels the resistance from the inner vessel wall. Such a risk is still present even if the locating members—as is stated in U.S. Pat. No. 6,368,341—are formed and shaped to minimize any potential damage to the blood vessel.

A more general problem encountered with closure devices of the type shown in U.S. Pat. No. 6,368,341 is the potential risk that a sealing member is deployed inside the blood vessel, instead of in the incision channel leading to the puncture hole in the vessel. This may for instance occur if a user misinterprets a resistance to retracting movement in the locating device as coming from the inner vessel wall, or accidentally pushes the whole haemostatic closure device too far into the incision channel before deploying the sealing member. The potential problem that a sealing member or a haemostatic material unintentionally is introduced into the vessel itself, instead of being positioned in the incision channel leading to the puncture hole in the vessel wall, can from a general point of view be ascribed to the fact that the closure devices known in the state of the art have access to the vessel through the puncture hole in the vessel wall.

This problem prevails also in U.S. Pat. No. 5,108,421, which is granted to Fowler and discloses how a vessel plug can be positioned against the outer surface of a vessel wall. During the positioning of the vessel plug, an inflated balloon is positioned against the inner surface of the vessel wall, thereby providing a support for the vessel plug and preventing the vessel plug from extending into the vessel. Nevertheless, the sealing member, here a vessel plug, has also in this case access to the vessel, and a user can by accident push the closure device too far into the incision channel and thereby deploy the sealing member inside the vessel.

In U.S. Pat. Nos. 5,391,183; 5,725,498; 5,741,223; 5,830,130; 5,948,425 and 6,325,789, all of which are granted to Janzen et al., devices are disclosed for inserting haemostatic material through a tissue channel and against the outside wall of a blood vessel, wherein the blood vessel wall has a puncture therein adjacent the tissue channel. Although the devices according to Janzen et al. have different designs, the same problem is encountered also here, i.e. that the haemostatic materials have access to the blood vessel through the puncture hole in the vessel wall.

Thus, there is a need in the art for a closure device that eliminates the risk that any sealing material unintentionally is introduced into a vessel. At the same time, the sealing material of such a closure device should not obstruct the fluid flow inside the vessel once the sealing operation has been completed.

The present invention discloses how a percutaneous incision leading to a vessel can be sealed without the risk that any sealing material unintentionally is introduced into the vessel itself. The closure device according to the present invention comprises basically an elongated insertion assembly and a charge of haemostatic material, which is contained in the distal portion of the insertion assembly. The insertion assembly, in turn, comprises a stationary part and a retractable part, which is in slidable engagement with the stationary part. The first step in a sealing operation is to connect the insertion assembly to the outside of an existing introducer, which already has been inserted into a vessel through an opening in the vessel wall in order to carry out the medical operation that made the percutaneous incision necessary. The insertion assembly is then slid along the introducer until it is in contact with the outer vessel wall. Thereafter, the charge of haemostatic material is delivered in the incision channel by retracting the retractable part of the insertion assembly. During this procedure, neither the insertion assembly nor the haemostatic material has access to the vessel itself, since the opening in the vessel wall is fully occupied by the inserted introducer. This eliminates the risk that the haemostatic material unintentionally is introduced into the vessel. Furthermore, the closure device has no parts that extend into the vessel, so the fluid flow inside the vessel remains unaffected after the completion of the sealing operation.

DETAILED DESCRIPTION OF THE PREFERRED EMBODIMENTS

Figure 1:
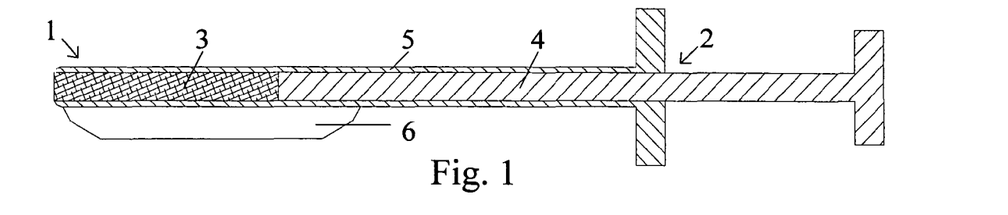
FIG. 1 shows schematically a first embodiment of a closure device according to the present invention.

In FIG. 1 is illustrated a first embodiment of a closure device 1 according to the present invention. The closure device 1 comprises an elongated insertion assembly 2 and a haemostatic or sealing material 3, which is contained in the distal portion of the insertion assembly 2. Preferably the haemostatic material 3 is impregnated or in some other way provided with a suitable clotting agent such as thrombin. The insertion assembly 2, in turn, comprises two parts, an elongated stationary part 4 and an elongated retractable part 5. Basically, the stationary part 4 has the shape of a rod, the distal end of which is in contact with the haemostatic material 3, and the retractable part 5 is in the form of a hollow sheath, which is in slidable engagement with the outside of the stationary part 4. Parts 4 and 5 may be made from any suitable material, such as plastic or metal. In FIG. 1, the closure device 1 is depicted in an initial state, with the distal portion of the retractable part 5 extending from the distal portion of the stationary part 4, thereby creating a space in which the haemostatic material 3 is accommodated. The proximal ends of the stationary part 4 and the retractable part 5 are advantageously provided with suitable handles, which extend perpendicular to the longitudinal axis of the insertion assembly 2 and which are adapted to facilitate the operation of the closure device 1. Such handles can have a variety of shapes and are not described in any detail. As mentioned above, a closure device according to the present invention is intended to be slidably attached to an existing introducer. This attachment can be accomplished by different attachment means, examples of which are described below. In this embodiment, the insertion assembly 2 comprises an attachment member 6, which is provided on the outside of the retractable part 5 and the function and form of which are described in more detail below.

Figure 2:
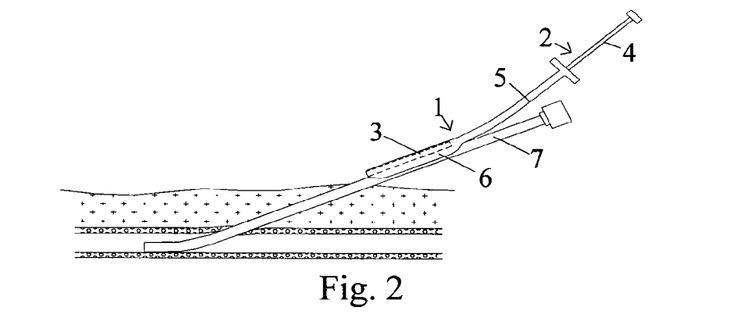
FIG. 2 illustrates schematically how the closure device of FIG. 1 is connected to an existing introducer in a first step of a sealing operation.

A closure device according to the present invention is designed for use in connection with an existing medical device such as an introducer. During use of the closure device, this introducer is in position in the percutaneous opening in the wall of the blood vessel. Consequently, neither the insertion assembly nor the haemostatic material has access to the blood vessel through the incision channel; which is in contrast to closure devices known in the state of the art. In FIG. 2 is illustrated how the attachment member 6 of the closure device 1 is attached to an introducer 7, the distal end of which has been inserted into a vessel through a puncture hole in the vessel wall. The introducer 7 is not a part of the present invention, and herein the term "introducer" is intended to encompass all types of medical devices having a distal portion that extends into a vessel and a proximal portion that extends out from a patient's skin (or other tissue). As should be apparent from the following description, such an introducer remains in position during the complete operation of the insertion assembly.

Figure 3:
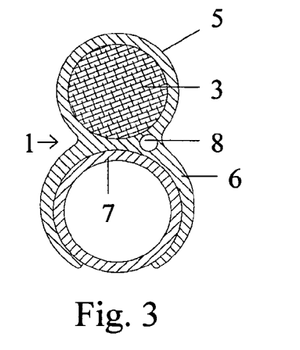
FIG. 3 shows the cross-section of the closure device and introducer of FIG. 2.

FIG. 3 shows the cross-section of the closure device 1 and the introducer 7 according to FIG. 2. In this embodiment, the closure device 1 is slidably connected to the introducer 7 by means of the attachment member 6, which is provided outside the distal portion of the retractable part 5. The attachment member 6 is generally tubular, with a slit extending along its length; thereby giving the distal portion of the closure device 1 a cross-section that has the general shape of the figure eight, with a portion being cut away at the base. From FIG. 2 and FIG. 3 it should be clear that the purpose of the slit is to make it possible to thread the attachment member 6 onto a tubular medical device, such as the introducer 7. By choosing a material with suitable flexibility (such as plastic) for the attachment member 6, it is possible to provide the closure device 1 with a dilatable attachment member 6, so that the closure device 1 can be attached to an introducer and then slid along the length of this introducer. The closure device 1 shown in FIG. 3 is further provided with a drip channel 8. The operations of the closure device 1 as well as the function of the drip channel 8 are going to be described in more detail below.

Referring again to FIG. 2, where the first step of a sealing operation is illustrated. Before this first step, a medical operation, such as a catheterization, on a patient has been completed, and an introducer 7, which was used during this medical operation, is still in position, i.e. the distal end of the introducer is inside a vessel, such as an artery, and the proximal end of introducer extends out of the patient's skin. In the first step of the sealing operation, the dilatable attachment member 6 is snapped onto the proximal end of the introducer 7. Thus, the insertion assembly 2 of the closure device 1 is now slidably connected to the introducer 7. In this state, the distal portion of the retractable part 5 extends from the distal portion of the stationary part 4, which leaves space enough to accommodate a charge of the haemostatic material 3 (indicated with dashed lines) in the distal portion of the insertion assembly 2.

Figure 4:
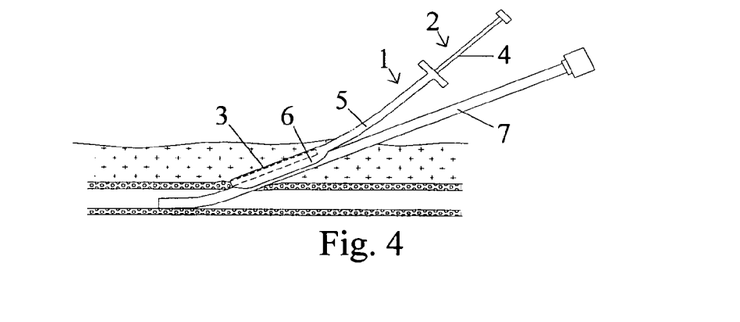
FIG. 4 illustrates the second step of the sealing operation.

FIG. 4 shows the completion of the second step in the sealing operation. In the second step, the insertion assembly 2, still being connected to the introducer 7 by means of the attachment member 6, is slid along the length of the introducer 7 until the distal end of the insertion assembly 2 is in contact with the outer surface of the vessel wall. When accomplishing this second step, a surgeon pushes the insertion assembly 2 through the incision channel, in which the introducer 7 is already positioned, thereby dilating the incision channel and compressing the surrounding tissue. If, for example, the sealing operation is performed at the femoral artery in the groin, the tissue surrounding the artery is mainly composed of adipose tissue, through which the insertion assembly 2 can be advanced relatively easily. Having in mind that vessel walls mainly are composed of fibrous tissue, which provides a significant resistance against further movement of the insertion assembly 2, the surgeon is provided with a readily detectable indication that the distal end of the insertion assembly 2 is in contact with the outer vessel wall. Furthermore, since the tissue in the edges of the dilated puncture hole in the vessel wall is in a stretched state, the risk that the insertion assembly 2 unintentionally is pushed through the puncture hole and into the vessel is minimal. In order to further reduce this risk, two more measures may be taken. These measures, which are to be described below, involve the drip channel mentioned above and an insertion assembly being provided with a distal tip that is bent upwards.

Figure 5:
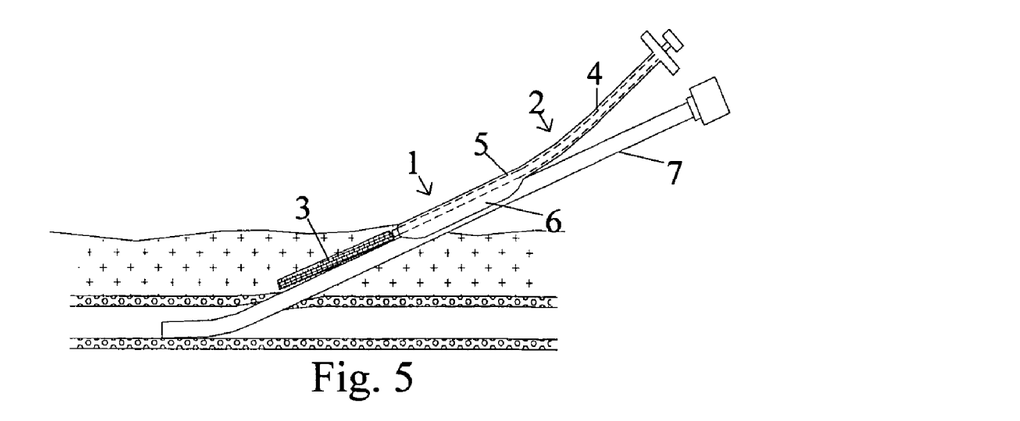
FIG. 5 illustrates the third step of the sealing operation.

In FIG. 5, the third step of the sealing operation has been completed. In the third step, the retractable part 5 is retracted over the stationary part 4 (indicated with dashed lines), thereby disengaging the haemostatic material 3 from the insertion assembly 2. Since the distal end of the stationary part 4 is in contact with the charge of haemostatic material 3, the haemostatic material 3 is prevented from being retracted by the retracting movement of the retractable part 5. When the third step of the sealing operation has been completed, the haemostatic material 3 is positioned in the incision channel leading to the puncture hole in the vessel wall. In this context it should be noted that the introducer 7 is still in position in the puncture hole in the vessel wall and there is no significant bleeding from the vessel.

Figure 6:
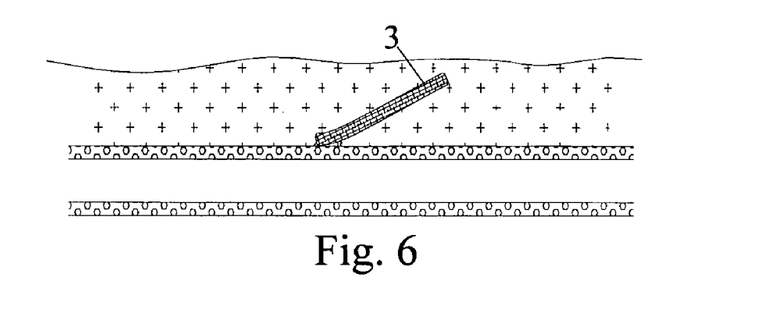
FIG. 6 illustrates the sealing member after the completion of the sealing operation.

FIG. 6 illustrates the completion of the fourth step in the sealing operation. In this final step, the closure device is slid backwards along the introducer and is then disconnected from the introducer and disposed of before the introducer is removed and disposed. As an alternative, the introducer may be retracted from the incision channel with the closure device still being connected. When the sealing operation has been completed, only the haemostatic material 3 is left in the incision channel, as is illustrated in FIG. 6. By providing the haemostatic material 3 with a suitable clotting agent, such as thrombin or chitosan, the time until complete haemostasis is achieved can be limited to a few minutes. If needed, applying an external pressure, either manually or by a suitable compression device, may assist the sealing operation.

Before finishing the discussion of the sealing operation, the special advantages with closure device according to the invention should be noted. During the above-described steps of the sealing operation, no parts of the closure device have had access to the vessel, and the positioning of the haemostatic material involves retracting movements only. Consequently, the risk that the haemostatic material of the closure device unintentionally is deployed inside the vessel is minimal; which is in contrast to closure devices known in the state of the art where a sealing member or a haemostatic material usually is positioned in the incision channel by means of a pushing movement in the forward direction, i.e. towards the opening in the vessel wall.

Figure 7:
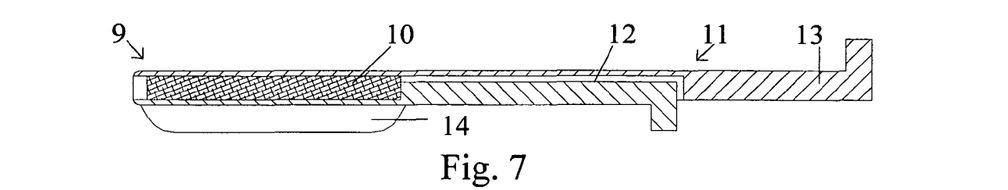
FIG. 7 shows schematically a second embodiment of a closure device in an initial state.

In the embodiment shown in FIG. 1, the retractable part 5 extends from the stationary part 4, or, with other words, the distal portion of the retractable part 5 constitutes the distal portion of the insertion assembly 2. Another embodiment of a closure device 9 is shown in FIG. 7. The closure device 9 comprises a haemostatic material 10 and an elongated insertion assembly 11, which comprises an elongated stationary part 12, an elongated retractable part 13 and an attachment member 14. The attachment member 14, which has the same shape as the attachment member 6 of the first embodiment, is attached to the outside of the stationary part 12. In this embodiment, the retractable part 13 has the general shape of a rod, which is provided with a recess that extends in the distal direction of the retractable part 13. The inner wall of the recess in the retractable part 13 is in slidable engagement with the proximal portion of the stationary part 12. The stationary part 12 has also the general shape of a rod, which is provided with a recess that extends in the distal direction of the stationary part 12. The recess in the stationary part 12 is shorter than the recess in the retractable part 13. In FIG. 7, the closure device 9 is depicted in an initial state, with the distal ends of the stationary part 12 and the retractable part 13 being in the same plane, i.e. the recess in the stationary part 12 and the recess in the retractable part 13 constitute together the distal portion of the insertion assembly 11 and provide the hollow space that contains the haemostatic material 10. The proximal end of the recess in the stationary part 12 is in contact with the haemostatic material 10, thereby preventing the haemostatic material 10 from being retracted by a retracting movement of the retractable part 13.

Whether or not the last feature, that the stationary part has a transverse portion, such as the end of a recess or the end of the stationary part, is essential for the closure device depends on the characteristics of the haemostatic material. For example, a haemostatic material in the form of a plug made from a solid material that easily slides inside the insertion assembly may require such a transverse portion, which prevents the plug from being retracted by the retracting movement of the retractable part. On the other hand, for a haemostatic material in the form of a sponge like material such a transverse portion may be redundant. Excluding a transverse portion may be advantageous in that different lengths of the charge of haemostatic material can be accommodated in the same insertion assembly.

Figure 8:
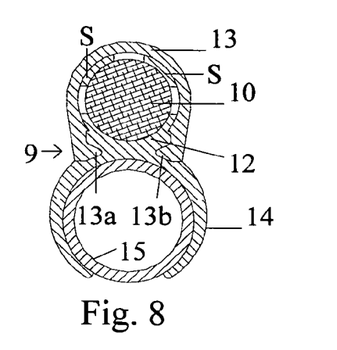
FIG. 8 shows the cross-section of the closure device of FIG. 7.

FIG. 8 shows the cross-section of the closure device 9, which is connected to an introducer 15 by means of the attachment member 14. The figure illustrates how the stationary part 12 and the retractable part 13 together provide the space in which the haemostatic material 10 is contained. FIG. 8 also shows spacers/guides S between retractable part 13 and haemostatic material 10. It can also be seen that the retractable part 13 is in slidable engagement with the stationary part 12 by means of projections 13a and 13b from the retractable part 13 that engage in grooves in the stationary part 12. Such projections and grooves may have a variety of different shapes. The attachment member 14 is attached to the distal portion of the stationary part 12, and a comparison of FIG. 8 with FIG. 3 reveals the difference between the attachment member 14 and the attachment member 6 of FIG. 3. Whereas the attachment member 6 is attached to the retractable part 5 of the closure device 1, the attachment member 14 is attached to the stationary part 12 of the closure device 9. This means that, during the retracting movement, the attachment member 14 remains in position on the introducer 15, which may facilitate a smooth operation of a closure device according to the present invention. Here it should be noted that instead of providing a single attachment member, a number of attachment members, e.g. in the form of flexible rings each provided with a slit, could be arranged spaced apart along the length of an insertion assembly.

Figure 9:
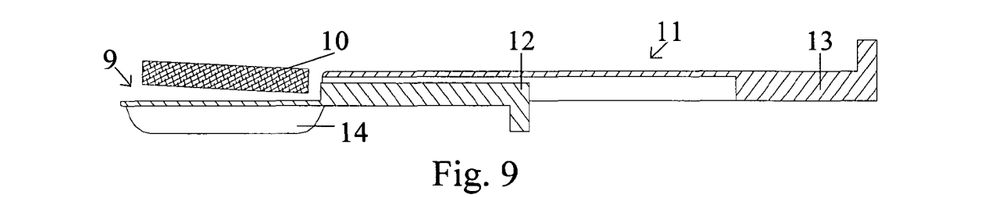
FIG. 9 shows the closure device of FIG. 7 in a disengaging state.

In FIG. 9, the closure device 9 is illustrated in a state that corresponds to the third step of the sealing operation described in connection with FIG. 5. In this third step, the retractable part 13 is retracted, which disengages the haemostatic material 10 from the insertion assembly 11. As can be seen from the figure, this retraction movement does not affect the attachment member 14, since it is connected to the stationary part 12. The introducer and the insertion assembly 11 are removed in a subsequent step.

Figure 10:
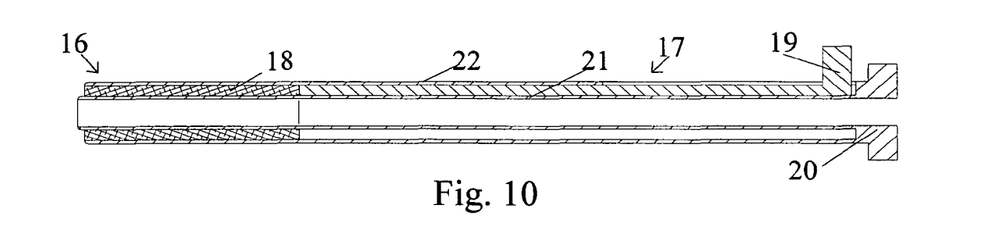
FIG. 10 shows schematically a third embodiment of a closure device.

In the embodiments shown in FIG. 1 and FIG. 7, respectively, the closure devices have been provided with an attachment means, such as attachment members 6 and 14, that virtually operates a separate part of the insertion assembly, i.e. the elongated insertion assembly slides as a separate part on the outside of the introducer. This is not to say that the attachment member actually is provided as a separate part to an existing insertion assembly, or that the attachment member has to be manufactured in a separate manufacturing step. In FIG. 10 is shown a third embodiment of a closure device 16. The closure device 16 comprises an elongated insertion assembly 17 and a charge of a haemostatic material 18. The insertion assembly 17, in turn, comprises an elongated stationary part 19 and an elongated retractable part 20. The retractable part 20 is in the form of a hollow sheath having an inner wall 21 and an outer wall 22. The charge of haemostatic material 18 is disposed between the inner wall 21 and the outer wall 22 in the distal portion of the retractable part 20. A slit 23 (not seen in the figure) extends along the length of the retractable part 20. The stationary part 19 has the general shape of a rod and is provided opposite to the slit 23 between the inner wall 21 and the outer wall 22, so that the retractable part 20 is in slidable engagement with the stationary part 19, and the distal end of the stationary part 19 is in contact with the proximal end of the charge of the haemostatic material 18. By means of this slit 23, which goes into the interior of the hollow retractable part 20, the insertion assembly 17 is slidably connected to an introducer, as is more easily recognized from FIG. 11.

Figure 11:
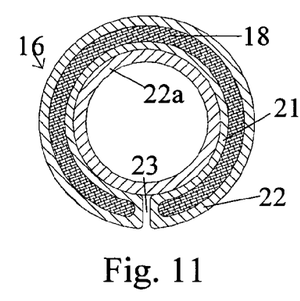
FIG. 11 shows the cross-section of the closure device of FIG. 10.

FIG. 11 shows the cross-section of the closure device 16 connected to an introducer 22a. In particular, the slit 23 is visible. By means of this slit 23 and by manufacturing the retractable part 20 from a flexible material (such as plastic), the retractable part 20 can be snapped onto an introducer, such as introducer 22a. Consequently, the slit 23 constitutes the attachment means for this embodiment of a closure device and replaces fastening means attached to the exterior of an insertion assembly. In this third embodiment, the slit 23 is only a narrow gap between the longitudinal edges of the hollow sheath that basically constitutes the retractable part 20. Further, the inner wall 21 and the outer wall 22 extend essentially all the way from the first longitudinal edge to the opposing second longitudinal edge, i.e. as much space as possible has been obtained for the haemostatic material 18.

Figure 12:
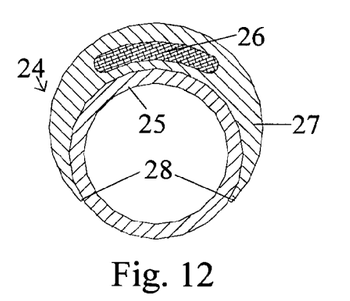
FIG. 12 shows the cross-section of a fourth embodiment of a closure device.

In FIG. 12 is shown the cross-section of a fourth embodiment of a closure device 24 connected to an introducer 25. The closure device 24 comprises a haemostatic material 26, which is contained in the distal portion of a retractable part 27. In this embodiment, the retractable part 27 has basically the form of a hollow sheath, with a rather large portion being cut away along its length. This cut-away portion (indicated with reference numeral 28) replaces the more narrow slit 23 described above in connection with FIG. 10 and FIG. 11. The wall of the hollow sheath that basically constitutes the retractable part 27 becomes thinner towards its longitudinal edges, thereby making it easy to thread the insertion assembly onto an introducer. Further, a cavity, which extends along the length of the retractable part 27, is provided opposite to the cut-away portion 28, where the wall of the retractable part 27 has its largest thickness. This cavity, in which the haemostatic material 26 is contained, occupies only a part of the circumference, i.e. the cavity does not extend all the way from the first longitudinal edge to the opposing second longitudinal edge.

Figure 13:
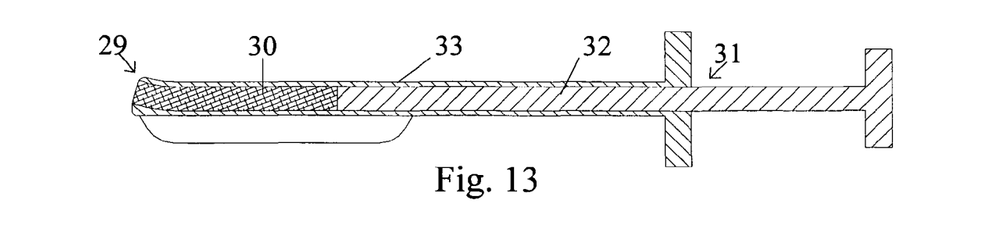
FIG. 13 shows schematically a fifth embodiment of a closure device.

As was mentioned above, two precautionary measures may be taken in order to further reduce the risk that an insertion assembly unintentionally is pushed through a vessel wall. The first of these measures is illustrated in FIG. 13, where a fifth embodiment of a closure device 29 is shown. The closure device 29 comprises a haemostatic material 30 and an insertion assembly 31, which, in turn, comprises a stationary part 32 and a retractable part 33. The insertion assembly 31 is similar to insertion assembly 2 shown in FIG. 1, except that the distal end of the insertion assembly 31 is slightly bent upwards. The purpose of this configuration is that the upwardly bent tip further reduces the risk that the insertion assembly 31 by accident is pushed through a vessel wall and into the vessel. It should be understood that all of the embodiments described above and illustrated in the figures could be provided with such an upwardly bent (or blunt) distal end, although an upwardly bent tip only has been explicitly shown for one embodiment of the invention.

Figure 14:
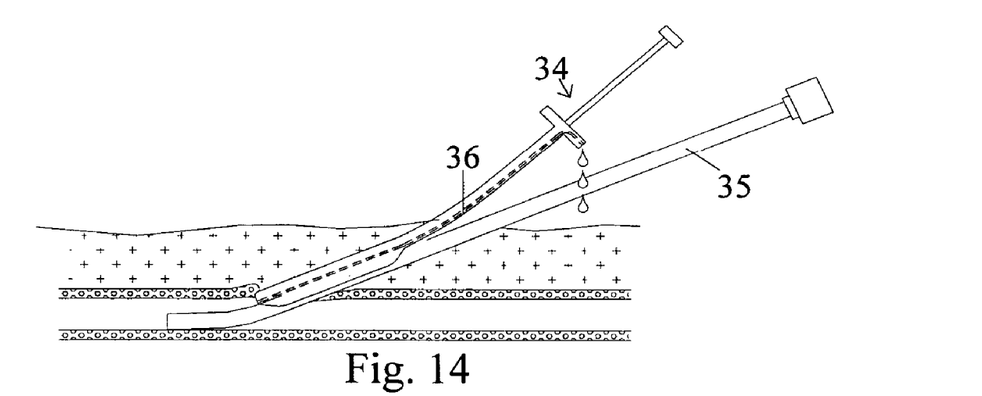
FIG. 14 illustrates a closure device that unintentionally has been introduced into a blood vessel and how this misplacement can be detected.

The second precautionary measure involves the drip channel 8 that was briefly mentioned in connection with FIG. 3. The function of such a drip channel is illustrated in FIG. 14, where an insertion assembly 34 has been attached to an introducer 35. The insertion assembly 34 is shown in a state where the insertion assembly 34 unintentionally has been pushed too far into the incision channel, so that the distal end of the insertion assembly has penetrated the vessel wall. The insertion assembly 34 is provided with a drip channel 36 (indicated with dashed lines) that extends from the distal end to the proximal end of the insertion assembly 34. As is illustrated in the figure, by means of the pressure that prevails inside the vessel, fluid is pressed into the inlet of the drip channel 36 and appears at the exit of the drip channel 36, thereby providing a user with a readily detectable indication that the insertion assembly 34 has penetrated the vessel wall. With other words, a requirement for a correctly positioned insertion assembly 34 is that there is essentially no fluid appearing from the proximal end of the drip channel 36. It should be understood that all of the embodiments described above and illustrated in the figures could be provided with a drip channel, although a drip channel only has been explicitly shown for one embodiment of the invention.

In conjunction with the different embodiments described and illustrated above, a haemostatic material has been said to be delivered in an incision canal by a retracting movement of a retractable part in relation to a stationary part and to an introducer, onto which an insertion assembly, comprising the stationary and retractable parts, has been snapped on. An important advantage with this way of delivering the haemostatic material is that there are no special physical requirements on the haemostatic material in this respect, i.e. the haemostatic material does not have to possess some inherent stiffness or "pushability" (i.e. resistance against compression) for allowing the haemostatic material to be pushed out of the insertion assembly and delivered in the incision canal. It is, however, within the scope of the present invention, that the haemostatic material is delivered by means of a pushing movement, in contrast to a retracting movement, as described and illustrated above.

Figure 15:
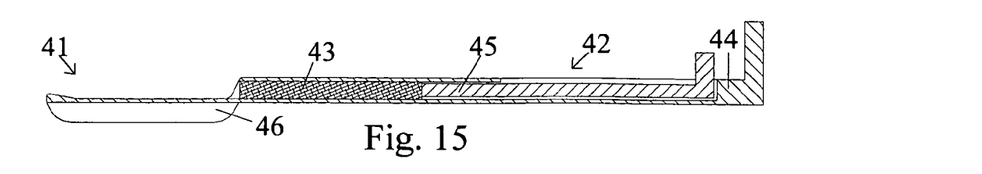
FIG. 15 shows schematically a sixth embodiment of a closure device.

In FIG. 15 is illustrated a sixth embodiment of a closure device 41 according to the present invention. The closure device 41 comprises an elongated insertion assembly 42 and a haemostatic or sealing material 43, which is contained in the insertion assembly 42. The insertion assembly 42, in turn, comprises an elongated stationary part 44, an elongated advanceable or pushable part 45, and an attachment member 46. In this embodiment, the attachment member 46 is of the same design as the attachment member 6 of FIG. 1 (or the attachment member 14 of FIG. 7). It should, however, be understood that an insertion assembly comprising an advanceable or pushable part could be combined with any of the attachment members already described above (e.g. in conjunction with FIG. 3, 8, 11 or 12), or be combined with any attachment member to be described below. In this embodiment, the advanceable part 45 has the general shape of a rod, the proximal end of which is provided with a handle of suitable shape. Except for its most distal portion, the stationary part 44 is generally tubular, with an inner diameter adapted to the outer diameter of the advanceable part 45, and has a longitudinal opening or slit in its wall at a proximal portion thereof. As should be clear from FIG. 15, the rod-shaped advanceable part 45 can thereby slide in the hollow portion of the stationary part 44, while the handle of the advanceable part 45 can slide in the longitudinal slit in the proximal portion of the stationary part 44.

Figure 16:
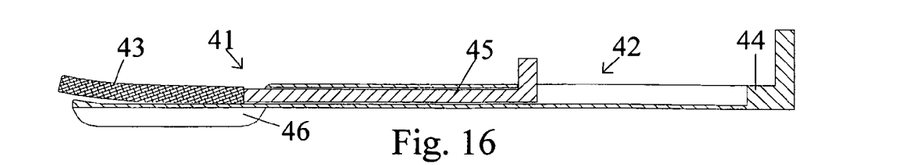
FIG. 16 shows the closure device of FIG. 15 in a disengaging state.

In FIG. 15, the closure device 41 is depicted in an initial state, with the haemostatic material 43 being contained in the hollow portion of the stationary part 44, and the distal end of the advanceable part 45 being in contact with the proximal end of the haemostatic material 43. In FIG. 16, the closure device 41 is illustrated in a state that corresponds to the third step of the sealing operation described above in connection with FIG. 5. In this third step, the advanceable part 45 is advanced (pushed) forward, which pushes the haemostatic material 43 out from the insertion assembly 42, such that the haemostatic material 43 is delivered in an incision channel. As can be seen from FIG. 16, this advancing movement does not affect the attachment member 46, since it is connected to the stationary part 44. The insertion assembly 42 is removed in a subsequent step.

A comparison between FIG. 9 and FIG. 16 reveals that a haemostatic material has been disengaged from an insertion assembly by means of a relative motion between a stationary part and a retractable part (as in FIG. 9), or between a stationary part and an advanceable part (as in FIG. 16). Strictly speaking, from FIGS. 9 and 16 alone, where no introducer is present—which it would be in use of a closure device—it is in fact impossible to tell which part has been moved forward and which part has been retracted. The skilled person should, however, have no difficulties in understanding what is meant. Nevertheless, from a practical point of view there is at least one significant difference between the two ways of delivering the haemostatic material. When the haemostatic material is released by a retracting movement of a retractable part, the haemostatic material does not have to possess any special physical properties, whereas a haemostatic material that is delivered by a pushing movement of an advanceable part has to possess a certain stiffness or resistance against compression such that the haemostatic material can be pushed out from an insertion assembly and advanced a distance in an incision canal. Although the latter way of delivering a haemostatic material puts additional requirements on the haemostatic material, a material delivery by a forward motion of a moveable part has also certain advantages, as will be explained below.

From FIG. 16 the reader may have noticed that the distal end of the haemostatic material 43 extends a certain distance beyond the distal end of the insertion assembly 42. This feature makes it possible to push the haemostatic material 43 into contact with a vessel wall, even though the distal end of the insertion assembly 42 for some reason has been located a small distance proximally of this vessel wall. It should further be realized—as is illustrated in, for example, FIG. 6—that an incision channel normally is created at a rather small angle to a vessel wall, i.e. the incision channel is far from being perpendicular to the vessel. The feature that a haemostatic material can be pushed some distance away from the distal end of an insertion assembly makes it thereby possibly for the haemostatic material to cover a larger area of the outer vessel wall, which can be very advantageous if the punctuation of the vessel wall has created a longitudinal wound that extends a distance along the vessel wall.

In FIGS. 15 and 16 it should also be noticed that the interior wall of the distal portion of the stationary part 44 ends in a slope pointing upwards, i.e., in use, away from the introducer. This feature, which also is to be seen in FIG. 13, has already been discussed before, but then in a different context. In combination with a pushing movement, a stationary part provided with a slightly inclined distal end makes it easier to position a small portion of a haemostatic material alongside of a vessel wall, rather than position the haemostatic material such that only the very distal end of the haemostatic material is in contact with the vessel wall. In other words, with an insertion assembly having a distal end that is bent upwards, or shaped such that the haemostatic material is delivered in an angle pointing away from the introducer, a larger contact area between the haemostatic material and the vessel wall is achieved something which is advantageous in some applications.

Figure 17:
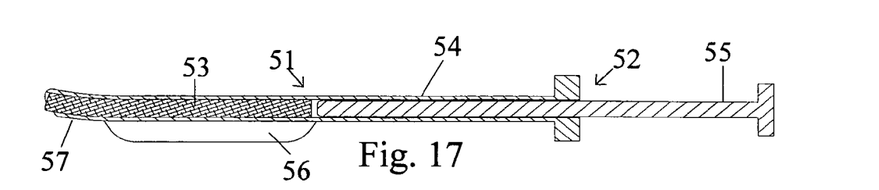
FIG. 17 shows schematically a seventh embodiment of a closure device.

The contact area between an outer vessel wall and a haemostatic material delivered by an insertion assembly according to the present invention can also be increased by other measures. FIG. 17 discloses a seventh embodiment of a closure device 51 according to the invention. The closure device 51 comprises an elongated insertion assembly 52 and a haemostatic material 53, which is contained in the distal portion of the insertion assembly 52. The insertion assembly 52, which comprises an elongated stationary part 54, an elongated pushable part 55, and an attachment member 56, is identical to the insertion assembly 2 shown in FIG. 1, except for the following distinguished features. In FIG. 1, the distal end of the attachment member 6 is almost even with the distal end of the insertion assembly 2 itself, whereas the attachment member 56 of FIG. 17 has been retracted a distance in the proximal direction of the insertion assembly 52. The insertion assembly 52 has thereby been provided with a protruding distal portion, herein called a "nose", which in FIG. 17 is indicated with the reference number 57. The nose 57 can be slightly bent upwards, as in FIG. 17, and/or can be made flexible or resilient. The purpose of such a nose 57 is further elucidated in conjunction with FIG. 18 below.

Figure 18:
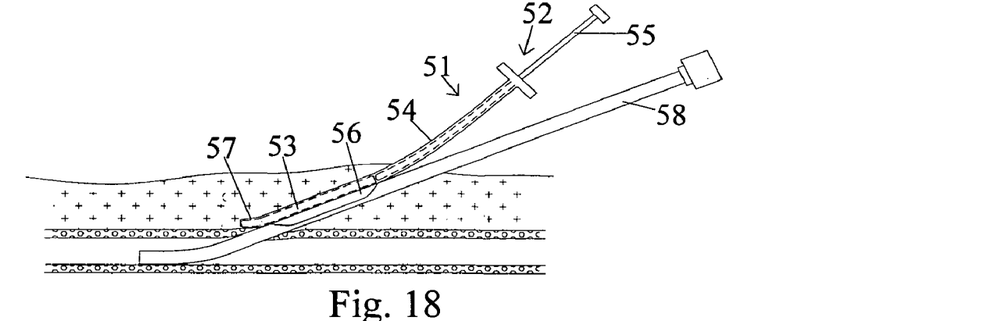
FIG. 18 illustrates the closure device of FIG. 17 in a state just before delivery of a haemostatic material.

FIG. 18 illustrates a situation wherein the closure device 51 of FIG. 17 has been attached to an introducer 58, and advanced along the introducer 58 into an incision canal created in a medical operation. The closure device 51 is shown in a state just before the haemostatic material 53 is delivered; and it should in particular be observed that the nose 57 of the insertion assembly 52 extends a distance along the vessel wall. A comparison between FIG. 4 and FIG. 18 should further clarify this function of the nose 57. Because of the retracted position of the attachment member 56 in relation to the distal end of the insertion assembly 52, the insertion assembly 52 has been provided with a protruding distal portion or nose 57. The nose 57 can be slightly bent upwards, and can preferably have a blunt end, which, even more preferred, is chamfered towards the attachment member 56, i.e. towards the introducer 58. The nose 57 can also be made from a flexible or resilient material. With these measures, and because of the inherent resilience of the vessel wall and the tissues surrounding the vessel, it is possible to position the nose 57 of the insertion assembly 52 along the vessel wall, rather than position a distal end of an insertion assembly abutting the vessel wall. This feature should be clear from the comparison between FIG. 18 and FIG. 4.

Figure 19:
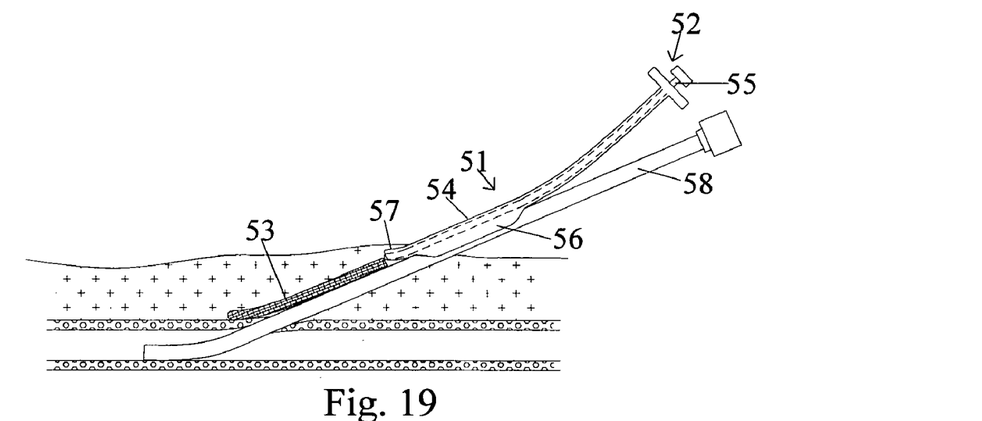
FIG. 19 illustrates the closure device of FIG. 17 in a state just after delivery of a haemostatic material.

When the insertion assembly 52 has been positioned in the incision canal, with the nose 57 of the insertion assembly 52 extending along the wall of a vessel, the haemostatic material 53 is pushed out from the insertion assembly 52 by advancing the pushable part 55 in relation to the stationary part 54. The insertion assembly 52 is subsequently retracted in a sliding motion along the introducer 58. This phase of the delivery operation is illustrated in FIG. 19. As an alternative, the insertion assembly 52 and the introducer 58 could be removed together, with the insertion assembly 52 still being positioned at the distal portion of the introducer 58. By providing the insertion assembly 52 with a nose 57, the contact area between the haemostatic material 53 and the vessel wall will be increased in comparison with, for example, the situation illustrated in FIG. 4. Here it should also be noted that the feature that an insertion assembly is provided with a nose is not limited to a closure device wherein the haemostatic material is delivered by a retracting movement of a retractable part. In other words, a nose can be combined with any of the embodiments described above, or with any of the embodiments to be described below.

Figure 20:
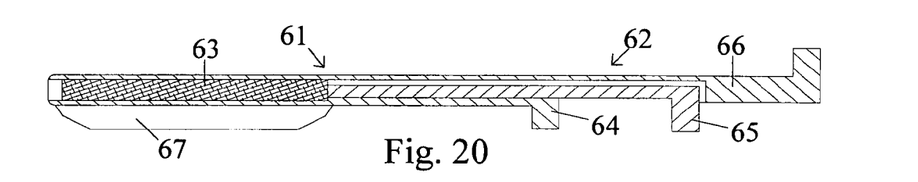
FIG. 20 shows schematically an eighth embodiment of a closure device in a first state.
Figure 21:
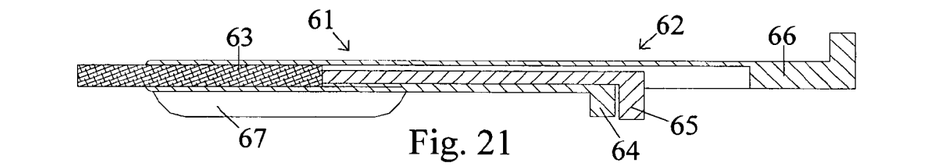
FIG. 21 shows the closure device of FIG. 20 in a second state.
Figure 22:
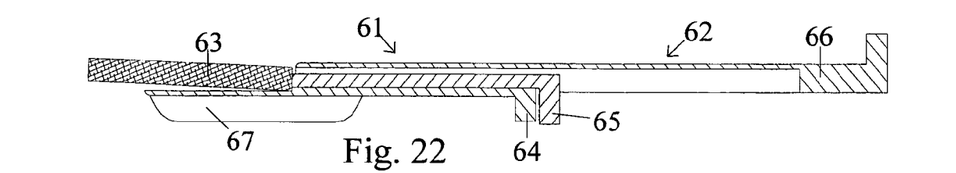
FIG. 22 shows the closure device of FIG. 20 in a third state.

Hitherto, two different ways of delivering a haemostatic material have been described: by means of a retracting movement and by means of a pushing movement, in both cases in relation to a stationary part and an introducer, onto which the stationary part has been attached. There are, however, more ways of delivering a haemostatic material in an incision canal without departing from the scope of the present invention. FIGS. 20, 21 and 22 illustrate three different states of an eighth embodiment of a closure device 61 according to the present invention. The closure device 61 comprises an elongated insertion assembly 62 and a haemostatic material 63, which is contained in a distal portion of the insertion assembly 62. The insertion assembly 62 comprises a stationary part 64, a pushable part 65, a retractable part 66, and an attachment member 67, which is attached to the stationary part 64. The attachment member 67 is of a previously described design, e.g. in conjunction with FIG. 1. The stationary part 64, pushable part 65 and retractable part 66 are, at their proximal ends, each provided with a separate handle of suitable shape. The retractable part 66 has the general shape of a rod, which is provided with a recess that extends in the distal direction of the retractable part 66. The stationary part 64 has also the general shape of a rod, which is provided with a recess that extends in the distal direction of the stationary part 64. The recess in the stationary part 64 is shorter than the recess in the retractable part 66. In FIG. 20, the closure device 61 is depicted in an initial or first state, with the distal ends of the stationary part 64 and retractable part 66 being in approximately the same plane, i.e. the recess in the stationary part 64 and the recess in the retractable part 66 constitute together the distal portion of the insertion assembly 62, and provide the hollow compartment that contains the haemostatic material 63. The proximal portion of the stationary part 64 is also provided with a recess, such that a longitudinal space is created between the inner wall of the stationary part 64 and the inner wall of the retractable part 66. The pushable part 65, which has the general shape of a rod, is slidable contained in this longitudinal space. The length of the recess in the retractable part 66 is adapted to the length of the haemostatic material 63 plus the length of the pushable part 65. As is illustrated in FIG. 20, with the pushable part 65 being in its retracted state, the haemostatic material 63 can thereby be accommodated in the distal portion of the insertion assembly 62, with the distal end of the pushable part 65 abutting the proximal end of the haemostatic material 63.

As already suggested by the description above, the closure device 61 combines a pushing movement and a retracting movement for delivering the haemostatic material 63. In FIG. 21, the closure device 61 is illustrated in a second state in which the pushable part 65 has been advanced within the longitudinal space created by the recesses in the stationary part 65 and retractable part 66, respectively. The distal end of the haemostatic material 63 has thereby been pushed out from the distal end of the insertion assembly 62, but a proximal portion of the haemostatic material 63 is still contained inside the insertion assembly 62.

FIG. 22 shows the closure device 61 in a third state. In this third state, the retractable part 66 is retracted, a movement that disengages the haemostatic material 63 from the insertion assembly 62. When the insertion assembly 62 is retracted, sliding on an introducer (not shown in the figure), the haemostatic material 63 is thereby left in an incision channel, as has been described and illustrated above. By combining a pushing movement with a retracting movement, the actual pushing length, i.e. the way that the haemostatic material has to be pushed in the incision canal, can be made very short. A comparison between, for example, FIG. 9 and FIG. 21 should clarify the latter statement. Having in mind that tissue surrounding an introducer, which has been introduced in an incision canal and has an insertion assembly attached thereon, contracts around the introducer and the insertion assembly, and thereby provides a rather large resistance against a forward motion of a haemostatic material, it is therefore easy to realize that a short advancing movement puts less requirement on the pushability of the haemostatic material.

Figure 23:
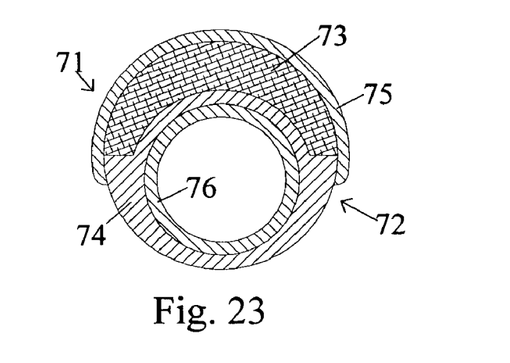
FIG. 23 shows schematically a cross-section of a ninth embodiment of a closure device in a first state.

A pushing movement or a retracting movement as well as a combination thereof are all examples of linear movements. A haemostatic material can also be delivered by another type of movement. In FIG. 23 is shown a cross-section of a closure device 71 according to a ninth embodiment of the present invention. The closure device 71 comprises an insertion assembly 72 and a haemostatic material 73. The insertion assembly 72 comprises a stationary part 74 and a turnable or rotatable part 75. At its distal portion, the stationary part 74 is provided with a recess, in which the haemostatic material 73 has been placed. The rotatable part 75 comprises an elongated body, whose distal portion has a semi-circular cross-section. The inner diameter of the rotatable part 75 is adapted to the nominal (as measured without the recess) outer diameter of the stationary part 74, such that the haemostatic material 73 can be contained within the space created between the stationary part 74 and the rotatable part 75. In FIG. 23, the closure device 71 has been attached to an introducer 76 in way that is not further specified, but it should be understood that a closure device comprising a turnable or rotatable part—with suitable modifications—could be combined with any of the attachment members described above, or with any of the attachment members to be described below.

Figure 24:
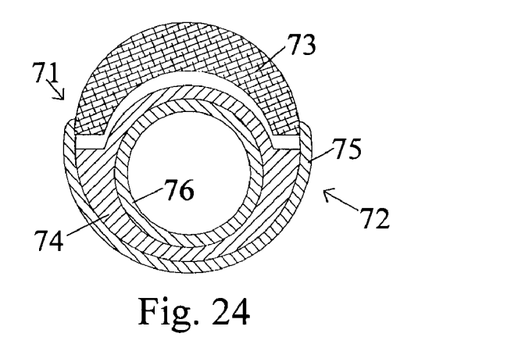
FIG. 24 shows the closure device of FIG. 23 in a disengaging state.

In FIG. 23 the closure device 71 is depicted in an initial state, with the haemostatic material 73 being covered by the rotatable part 75. FIG. 24 illustrates the closure device 71 in a second, disengaging state. In this state, the rotatable part 75 is rotated in relation to the stationary part 74 and the introducer 76, such that the haemostatic material 73 no longer is covered by the rotatable part 75. When the haemostatic material 73 in this way has been released, the introducer assembly 72 is retracted in a subsequent step, either together with the introducer 76, or sliding along the introducer 76.

Figure 25:
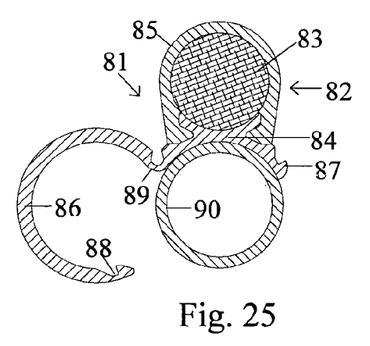
FIG. 25 illustrates schematically a cross-section of a tenth embodiment of a closure device comprising an attachment member shown in an open state.

Above, several different types of attachment members have been illustrated and described, e.g. in conjunction with FIGS. 3, 8, 11, 12 and 17. A common feature of these attachment members is that they are snapped on an introducer by means of a slit or cut-away portion extending longitudinally in an attachment member arranged as a separate member (as in FIGS. 3, 8 and 17), or enveloping the introducer assembly itself (as in FIGS. 11 and 12). As mentioned above, the material in which such a slit or cut-away portion has been made must then be flexible or resilient. Consequently, the capability of these types of attachment members to stay securely but slidably attached to an introducer, onto which the attachment member in question has been snapped on, depends mainly on the characteristics of the material. A somewhat different way of attaching a closure device to an introducer is disclosed in FIGS. 25 and 26, where a tenth embodiment of a closure device 81 according to the present invention is presented. The closure device 81 has the same general design as the closure device 9 illustrated in FIG. 7, with a haemostatic material 83 contained in an insertion assembly 82 comprising a stationary part 84 and a retractable part 85. The insertion assembly 82 of FIG. 25 is, however, provided with an attachment member 86, which exhibits important differences in comparison with the attachment member 14 of FIG. 7. The attachment member 86 has a generally circular cross-section. The attachment member 86 is, however, not closed, but is divided such that two ends are formed. One of these ends is provided with a lip 87, which fits into a notch 88 provided in the other, opposite end. The attachment member 86 has at least one flexible portion 89, which can act as a hinge. In FIG. 25, the attachment member 86 is illustrated in an open position, wherein the attachment member 86, due to the hinge action of the flexible portion 89, has been bent away from an introducer 90, along the mantle of which the insertion assembly 82 has been positioned.

Figure 26:
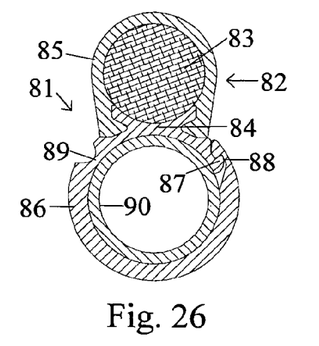
FIG. 26 shows the closure device of FIG. 25, with the attachment member in a closed state.

In FIG. 26, the attachment member 86 is shown in a closed position. To close the attachment member 86, the two ends of the attachment member 86 are brought together—whereby the flexible portion 89 acts as a hinge—until the lip 87 at the first end is hooked into the notch 88 in the second, opposite end. The attachment member 86 is thereby bent and securely locked around the introducer 90. The diameter of the now closed ring-shaped attachment member 86 is slightly larger than the outer diameter of the introducer 90, such that the attachment member 86 is slidably attached to the introducer 90. Several short attachment members of this type can be provided along the length of an introducer, or a single attachment member of this type can be long enough to enclose a suitable length of an introducer. Instead of providing a flexible portion acting as a hinge, a real hinge could be provided. Also the locking mechanism can be in the form of a more elaborate construction, such as a tap and hole, or a locking mechanism involving a hook and eye.

The attachment member 86 of FIGS. 25 and 26 differs from the attachment members previously described in that the attachment member 86 relies on a special locking mechanism—here a lip 87 and a notch 88—for securing the insertion assembly 82 to the introducer 90, rather than provide a slit or opening in an attachment member and then rely on the resistance of the material for securing an insertion assembly to an introducer. An object of the present invention is to provide a closure device which eliminates the risk that sealing material unintentionally is introduced into a vessel. A key feature of the closure device is that it can be attached to a proximal portion of an introducer, a distal portion of which extends in an incision canal. These requirements are fulfilled also with an attachment member having a locking mechanism similar to the type shown in FIGS. 25 and 26, and hence a closure device can be provided with a locking attachment member without departing from the scope of the present invention. A locking type of attachment member could be combined with an insertion assembly comprising a stationary part together with a retracting part and/or an advanceable part and/or a rotatable part.

Figure 27:
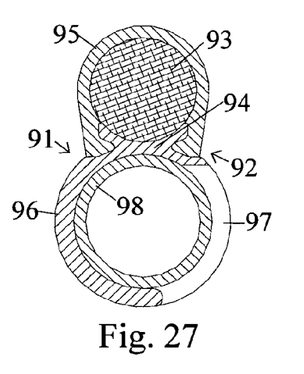
FIGS. 27 to 29 show three different views of an eleventh embodiment of a closure device.
Figure 28:
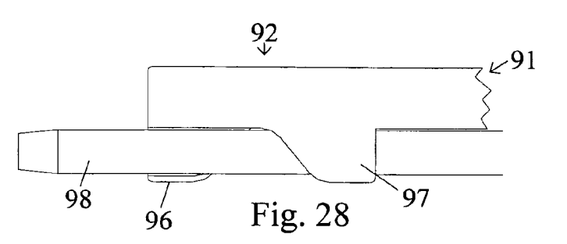
Figure 29:
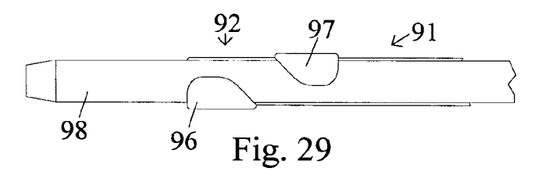

A further way of attaching a closure device to an introducer is illustrated in FIGS. 27, 28 and 29, wherein an eleventh embodiment of a closure device 91 is illustrated in three different views. As perhaps best seen in FIG. 27, the closure device 91 comprises an insertion assembly 92 and a haemostatic material 93, which is contained in the insertion assembly 92. The insertion assembly 92 comprises a stationary part 94 and a retractable part 95, the functions of which are the same as in the insertion assembly 11 of FIG. 9. In FIG. 27, the insertion assembly 92 has been attached to an introducer 98 by means of a first attachment member 96 and a second attachment member 97, which are provided on the insertion assembly 92. As is best seen in FIGS. 28 and 29, the first attachment member 96 has the shape of a semi-circular lug, and is arranged at the distal end of the insertion assembly 92. The second attachment member 97 has also the shape of a semi-circular lug, and is arranged proximally of the first attachment member 96. Although longitudinally spaced apart, the concave side of the first attachment member 96 is pointing towards the concave side of the second attachment member 97, such that an imaginary line connecting the respective centre of curvature for the attachment members 96, 97 runs in parallel with the insertion assembly 92.

When the closure device 91 is to be connected to the introducer 98, the insertion assembly 92 is positioned over the introducer 98, such that the introducer 98 is located between the first and second attachment members 96, 97. In this state (not shown in the figures), the longitudinal axis of the insertion assembly 92 is thereby rotated with respect to the longitudinal axis of the introducer 98. In a subsequent step, the insertion assembly 92 is rotated such that the first and second attachment members 96, 97 engage the introducer 98, i.e. the insertion assembly 92 is positioned in parallel with the introducer 98, in the way illustrated in FIGS. 27, 28 and FIG. 29. This kind of attachment, comprising a "rotate-and-lock" function, is also within the scope of the present invention, and can be combined with an insertion assembly comprising a stationary part together with a retracting part and/or an advanceable part and/or a rotatable part. It should further be understood that the radius of curvatures of the attachment members 96, 97 are adapted to the diameter of the introducer 98 such that the insertion assembly 92 is slidably attached to the introducer 98. Moreover, attachment members having the above-mentioned "rotate-and-lock" function could be differently oriented with respect to an insertion assembly. It is, for example, possible that the concave side of one lug is directed towards the insertion assembly, while the concave side of the other lug is directed away from the insertion assembly, the important feature being that the concave sides—although longitudinally displaced—are pointing towards each other.

Although the present invention has been described with reference to specific embodiments, also shown in the appended drawings, it will be apparent for those skilled in the art that many variations and modifications can be done within the scope of the invention as described in the specification and defined with reference to the following claims.

What is claimed is:

1. A closure device for sealing an incision channel extending from a tissue surface of a patient, through a wall of a vessel and into the vessel, in conjunction with a hollow introducer having a hollow interior that provides access to the vessel and whose proximal end is outside the tissue surface, said closure device comprising:
   a haemostatic material;
   a stationary member;
   a moveable member;
   at least one attachment mechanism, the attachment mechanism including an opening such that the attachment mechanism is connectable to the hollow introducer and off-set to a side of the hollow introducer;
   a sliding surface configured such that the closure device is slidable along the hollow introducer; and
   wherein the haemostatic material, the stationary member, and the moveable member are configured such that the haemostatic material is delivered in the incision channel by moving at least the moveable member relative to the stationary member;
   wherein the attachment mechanism is configured to attach to a portion of the hollow introducer that has a continuous cylindrical outer surface;
   wherein the attachment mechanism is configured to releasably attach to the portion of the hollow introducer that has the continuous cylindrical outer surface;
   wherein the attachment mechanism is located at a distal end of the closure device and the haemostatic material is located at the distal end of the closure device before the closure device is attached to the hollow introducer.

2. A closure device as set forth in claim 1, wherein the haemostatic material is delivered in the incision channel by retracting the moveable member.

3. A closure device as set forth in claim 1, wherein the haemostatic material is delivered in the incision channel by pushing the moveable member toward the distal end of the closure device.

4. A closure device as set forth in claim 1, wherein the haemostatic material is delivered in the incision channel by rotating the moveable member.

5. A closure device as set forth in claim 1, wherein the attachment mechanism comprises a member to open and close the opening.

6. A closure device as set forth in claim 1, wherein the attachment mechanism comprises at least one semi-circular lug.

7. A closure device as set forth in claim 6, further comprising a second semi-circular lug.

8. A closure device as set forth in claim 1, wherein the distal end of the closure device is bent in a direction away from a longitudinal axis of the hollow introducer.

9. A closure device as set forth in claim 1, wherein the closure device comprises a protruding distal portion which is distal of the attachment mechanism.

10. A closure device as set forth in claim 1, wherein the closure device is configured such that the haemostatic material is deliverable distally from the distal end of the closure device.

11. A closure device as set forth in claim 1, further comprising a third member such that the haemostatic material is delivered in the incision channel by pushing the moveable member toward the distal end of the closure device and retracting the third member toward a proximal end of the closure device.

12. A closure device as set forth in claim 1, wherein the closure device includes a drip channel.

13. A closure device as set forth in claim 1, wherein the distal end of the closure device is bent upwardly away from a longitudinal axis of the closure device.

14. A closure device as set forth in claim 1, wherein a distal end of the moveable member is configured to directly contact an outer wall of the vessel to provide an indication that the closure device is in contact with the outer wall.

* * * * *